US009339274B2

(12) United States Patent
Dakin

(10) Patent No.: US 9,339,274 B2
(45) Date of Patent: May 17, 2016

(54) PARAVALVULAR LEAK OCCLUSION DEVICE FOR SELF-EXPANDING HEART VALVES

(71) Applicant: AGA Medical Corporation, Plymouth, MN (US)

(72) Inventor: Gregory James Dakin, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 172 days.

(21) Appl. No.: 13/797,513

(22) Filed: Mar. 12, 2013

(65) Prior Publication Data

US 2014/0277425 A1 Sep. 18, 2014

(51) Int. Cl.
*A61B 17/08* (2006.01)
*A61B 17/12* (2006.01)
(Continued)

(52) U.S. Cl.
CPC ..... *A61B 17/12122* (2013.01); *A61B 17/12172* (2013.01); *A61B 17/12118* (2013.01); *A61F 2/2418* (2013.01); *A61F 2002/077* (2013.01); *A61F 2250/0069* (2013.01)

(58) Field of Classification Search
CPC ....... A61F 2/24; A61F 2/2409; A61F 2/2412; A61F 2/2418; A61F 2/2427; A61F 2/243; A61F 2/2433; A61F 2/2436; A61F 2/2439; A61F 2/246; A61F 2220/0083; A61F 2002/821; A61F 2002/823; A61F 2/82; A61F 2/86; A61F 2/856; A61F 2/88; A61F 2/89; A61F 2/90; A61F 2/915; A61F 2002/91508–2002/91591; A61B 17/12122; A61B 17/12022; A61B 17/12036; A61B 17/12109; A61B 17/12113; A61B 17/12136; A61B 17/1214; A61B 17/12145; A61B 17/1215; A61B 17/12154; A61B 17/12168; A61B 17/12172; A61B 17/12177
USPC ............... 604/96.01; 606/158, 191, 192, 194, 606/195, 198; 623/2.1–2.35
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 A1 | 11/2002 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — Jonathan W Miles
*Assistant Examiner* — Kankindi Rwego
(74) *Attorney, Agent, or Firm* — Lerner, David, Littenberg, Krumholz & Mentlik, LLP

(57) ABSTRACT

An occluder for sealing gaps between a medical device and adjacent body tissue includes an expandable body configured to fill the gaps between the medical device and the body tissue. The occluder includes a fastener at one end of the body and adapted to couple to a first end of the medical device, and an expandable disk at the other end of the body and adapted to couple to the medical device at a position spaced from the first end.

20 Claims, 9 Drawing Sheets

(51) Int. Cl.
    *A61F 2/24* (2006.01)
    *A61F 2/07* (2013.01)

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,420,016 A | 5/1995 | Boguslaski et al. | |
| 5,480,423 A | 1/1996 | Ravenscroft et al. | |
| 5,843,167 A | 12/1998 | Dwyer et al. | |
| 5,846,261 A * | 12/1998 | Kotula et al. | 606/213 |
| 5,855,601 A | 1/1999 | Bessler et al. | |
| 5,935,163 A | 8/1999 | Gabbay | |
| 5,961,549 A | 10/1999 | Nguyen et al. | |
| 6,041,785 A | 3/2000 | Webb | |
| 6,045,576 A | 4/2000 | Starr et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,652,578 B2 | 11/2003 | Bailey et al. | |
| 6,685,625 B2 | 2/2004 | Gabbay | |
| 6,716,244 B2 | 4/2004 | Klaco | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 6,951,573 B1 | 10/2005 | Dilling | |
| 6,986,786 B1 * | 1/2006 | Smith | 623/1.36 |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,195,641 B2 | 3/2007 | Palmaz et al. | |
| 7,247,167 B2 | 7/2007 | Gabbay | |
| 7,267,686 B2 | 9/2007 | DiMatteo et al. | |
| 7,276,078 B2 * | 10/2007 | Spenser et al. | 623/1.24 |
| 7,311,730 B2 | 12/2007 | Gabbay | |
| 7,320,704 B2 | 1/2008 | Lashinski et al. | |
| 7,329,278 B2 | 2/2008 | Seguin et al. | |
| 7,374,573 B2 | 5/2008 | Gabbay | |
| 7,381,218 B2 | 6/2008 | Schreck | |
| 7,381,219 B2 | 6/2008 | Salahieh et al. | |
| 7,452,371 B2 | 11/2008 | Pavcnik et al. | |
| 7,510,572 B2 | 3/2009 | Gabbay | |
| 7,510,575 B2 | 3/2009 | Spenser et al. | |
| 7,524,331 B2 | 4/2009 | Birdsall | |
| 7,534,261 B2 | 5/2009 | Friedman | |
| RE40,816 E | 6/2009 | Taylor et al. | |
| 7,585,321 B2 | 9/2009 | Cribier | |
| 7,628,805 B2 | 12/2009 | Spenser et al. | |
| 7,682,390 B2 | 3/2010 | Seguin | |
| 7,708,775 B2 | 5/2010 | Rowe et al. | |
| 7,731,742 B2 | 6/2010 | Schlick et al. | |
| 7,748,389 B2 | 7/2010 | Salahieh et al. | |
| 7,780,725 B2 | 8/2010 | Haug et al. | |
| 7,799,069 B2 | 9/2010 | Bailey et al. | |
| 7,803,185 B2 | 9/2010 | Gabbay | |
| 7,824,442 B2 | 11/2010 | Salahieh et al. | |
| 7,837,727 B2 | 11/2010 | Goetz et al. | |
| 7,846,203 B2 | 12/2010 | Cribier | |
| 7,846,204 B2 | 12/2010 | Letac et al. | |
| 7,892,281 B2 | 2/2011 | Seguin et al. | |
| 7,914,569 B2 | 3/2011 | Nguyen et al. | |
| 7,959,666 B2 | 6/2011 | Salahieh et al. | |
| 7,959,672 B2 | 6/2011 | Salahieh et al. | |
| 7,972,378 B2 | 7/2011 | Tabor et al. | |
| 7,988,724 B2 | 8/2011 | Salahieh et al. | |
| 7,993,394 B2 | 8/2011 | Hariton et al. | |
| 8,016,877 B2 | 9/2011 | Seguin et al. | |
| D648,854 S | 11/2011 | Braido | |
| 8,048,153 B2 | 11/2011 | Salahieh et al. | |
| 8,052,741 B2 | 11/2011 | Bruszewski et al. | |
| 8,052,749 B2 | 11/2011 | Salahieh et al. | |
| 8,052,750 B2 | 11/2011 | Tuval et al. | |
| 8,062,355 B2 | 11/2011 | Figulla et al. | |
| 8,075,611 B2 | 12/2011 | Millwee et al. | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| 8,137,398 B2 | 3/2012 | Tuval et al. | |
| 8,142,497 B2 | 3/2012 | Friedman | |
| D660,432 S | 5/2012 | Braido | |
| D660,433 S | 5/2012 | Braido et al. | |
| D660,967 S | 5/2012 | Braido et al. | |
| 8,182,528 B2 | 5/2012 | Salahieh et al. | |
| 8,221,493 B2 | 7/2012 | Boyle et al. | |
| 8,230,717 B2 | 7/2012 | Matonick | |
| 8,231,670 B2 | 7/2012 | Salahieh et al. | |
| 8,252,051 B2 | 8/2012 | Chau et al. | |
| 8,308,798 B2 | 11/2012 | Pintor et al. | |
| 8,313,525 B2 | 11/2012 | Tuval et al. | |
| 8,323,335 B2 | 12/2012 | Rowe et al. | |
| 8,323,336 B2 | 12/2012 | Hill et al. | |
| 8,343,213 B2 | 1/2013 | Salahieh et al. | |
| 8,348,995 B2 | 1/2013 | Tuval et al. | |
| 8,348,996 B2 | 1/2013 | Tuval et al. | |
| 8,348,998 B2 | 1/2013 | Pintor et al. | |
| 8,366,769 B2 | 2/2013 | Huynh et al. | |
| 8,403,983 B2 | 3/2013 | Quadri et al. | |
| 8,408,214 B2 | 4/2013 | Spenser | |
| 8,414,643 B2 | 4/2013 | Tuval et al. | |
| 8,425,593 B2 | 4/2013 | Braido et al. | |
| 8,449,599 B2 | 5/2013 | Chau et al. | |
| 8,449,604 B2 | 5/2013 | Moaddeb et al. | |
| 8,454,686 B2 | 6/2013 | Alkhatib | |
| 8,500,798 B2 | 8/2013 | Rowe et al. | |
| 8,568,474 B2 | 10/2013 | Yeung et al. | |
| 8,579,962 B2 | 11/2013 | Salahieh et al. | |
| 8,579,966 B2 | 11/2013 | Seguin et al. | |
| 8,585,755 B2 | 11/2013 | Chau et al. | |
| 8,591,575 B2 | 11/2013 | Cribier | |
| 8,597,349 B2 | 12/2013 | Alkhatib | |
| 8,603,159 B2 | 12/2013 | Seguin et al. | |
| 8,603,160 B2 | 12/2013 | Salahieh et al. | |
| 8,613,765 B2 | 12/2013 | Bonhoeffer et al. | |
| 8,623,074 B2 | 1/2014 | Ryan | |
| 8,652,204 B2 | 2/2014 | Quill et al. | |
| 8,663,322 B2 | 3/2014 | Keranen | |
| 8,668,733 B2 | 3/2014 | Haug et al. | |
| 8,685,080 B2 | 4/2014 | White | |
| 8,728,154 B2 | 5/2014 | Alkhatib | |
| 8,747,459 B2 | 6/2014 | Nguyen et al. | |
| 8,764,820 B2 | 7/2014 | Dehdashtian et al. | |
| 8,795,357 B2 | 8/2014 | Yohanan et al. | |
| 8,801,776 B2 | 8/2014 | House et al. | |
| 8,808,356 B2 | 8/2014 | Braido et al. | |
| 8,828,078 B2 | 9/2014 | Salahieh et al. | |
| 8,834,563 B2 | 9/2014 | Righini | |
| 8,840,663 B2 | 9/2014 | Salahieh et al. | |

(56) References Cited

U.S. PATENT DOCUMENTS

| | | | |
|---|---|---|---|
| 8,876,894 | B2 | 11/2014 | Tuval et al. |
| 8,876,895 | B2 | 11/2014 | Tuval et al. |
| 8,940,040 | B2 | 1/2015 | Shahriari |
| 8,945,209 | B2 | 2/2015 | Bonyuet et al. |
| 8,961,595 | B2 | 2/2015 | Alkhatib |
| 8,974,523 | B2 | 3/2015 | Thill et al. |
| 8,974,524 | B2 | 3/2015 | Yeung et al. |
| 2002/0036220 | A1 | 3/2002 | Gabbay |
| 2003/0023303 | A1 | 1/2003 | Palmaz et al. |
| 2003/0050694 | A1 | 3/2003 | Yang et al. |
| 2003/0130726 | A1 | 7/2003 | Thorpe et al. |
| 2004/0044391 | A1* | 3/2004 | Porter ............... 623/1.1 |
| 2004/0049262 | A1 | 3/2004 | Obermiller et al. |
| 2004/0093075 | A1 | 5/2004 | Kuehne |
| 2004/0111111 | A1 | 6/2004 | Lin |
| 2004/0210304 | A1 | 10/2004 | Seguin et al. |
| 2004/0260389 | A1 | 12/2004 | Case et al. |
| 2005/0096726 | A1 | 5/2005 | Sequin et al. |
| 2005/0137682 | A1 | 6/2005 | Justino |
| 2005/0137695 | A1 | 6/2005 | Salahieh et al. |
| 2005/0137697 | A1 | 6/2005 | Salahieh et al. |
| 2005/0203605 | A1 | 9/2005 | Dolan |
| 2005/0256566 | A1 | 11/2005 | Gabbay |
| 2006/0008497 | A1 | 1/2006 | Gabbay |
| 2006/0074484 | A1 | 4/2006 | Huber |
| 2006/0122692 | A1 | 6/2006 | Gilad et al. |
| 2006/0149360 | A1 | 7/2006 | Schwammenthal et al. |
| 2006/0161249 | A1 | 7/2006 | Realyvasquez et al. |
| 2006/0173532 | A1 | 8/2006 | Flagle et al. |
| 2006/0178740 | A1 | 8/2006 | Stacchino et al. |
| 2006/0195181 | A1 | 8/2006 | Johnson et al. |
| 2006/0206202 | A1 | 9/2006 | Bonhoeffer et al. |
| 2006/0241744 | A1 | 10/2006 | Beith |
| 2006/0241745 | A1 | 10/2006 | Solem |
| 2006/0259120 | A1 | 11/2006 | Vongphakdy et al. |
| 2006/0259137 | A1 | 11/2006 | Artof et al. |
| 2006/0265056 | A1 | 11/2006 | Nguyen et al. |
| 2006/0276813 | A1 | 12/2006 | Greenberg |
| 2006/0276874 | A1 | 12/2006 | Wilson et al. |
| 2006/0287717 | A1 | 12/2006 | Rowe et al. |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0050012 | A1* | 3/2007 | Densford ............... 623/1.23 |
| 2007/0055355 | A1* | 3/2007 | Kim et al. ............... 623/1.21 |
| 2007/0055358 | A1 | 3/2007 | Krolik et al. |
| 2007/0067029 | A1 | 3/2007 | Gabbay |
| 2007/0093890 | A1 | 4/2007 | Eliasen et al. |
| 2007/0100435 | A1 | 5/2007 | Case et al. |
| 2007/0118210 | A1 | 5/2007 | Pinchuk |
| 2007/0213813 | A1 | 9/2007 | Von Segesser et al. |
| 2007/0233228 | A1 | 10/2007 | Eberhardt et al. |
| 2007/0244545 | A1 | 10/2007 | Birdsall et al. |
| 2007/0244552 | A1 | 10/2007 | Salahieh et al. |
| 2007/0288087 | A1 | 12/2007 | Fearnot et al. |
| 2008/0021552 | A1 | 1/2008 | Gabbay |
| 2008/0039934 | A1 | 2/2008 | Styrc |
| 2008/0071369 | A1 | 3/2008 | Tuval et al. |
| 2008/0082164 | A1 | 4/2008 | Friedman |
| 2008/0097595 | A1 | 4/2008 | Gabbay |
| 2008/0114452 | A1 | 5/2008 | Gabbay |
| 2008/0125853 | A1 | 5/2008 | Bailey et al. |
| 2008/0140189 | A1 | 6/2008 | Nguyen et al. |
| 2008/0147183 | A1 | 6/2008 | Styrc |
| 2008/0154355 | A1 | 6/2008 | Benichou et al. |
| 2008/0154356 | A1 | 6/2008 | Obermiller et al. |
| 2008/0243245 | A1 | 10/2008 | Thambar et al. |
| 2008/0255662 | A1 | 10/2008 | Stacchino et al. |
| 2008/0262602 | A1 | 10/2008 | Wilk et al. |
| 2008/0269879 | A1 | 10/2008 | Sathe et al. |
| 2009/0099653 | A1 | 4/2009 | Suri et al. |
| 2009/0112309 | A1 | 4/2009 | Jaramillo et al. |
| 2009/0138079 | A1 | 5/2009 | Tuval et al. |
| 2009/0276027 | A1 | 11/2009 | Glynn |
| 2010/0004740 | A1 | 1/2010 | Seguin et al. |
| 2010/0036484 | A1 | 2/2010 | Hariton et al. |
| 2010/0049306 | A1 | 2/2010 | House et al. |
| 2010/0087907 | A1 | 4/2010 | Lattouf |
| 2010/0131055 | A1 | 5/2010 | Case et al. |
| 2010/0168778 | A1 | 7/2010 | Braido |
| 2010/0168839 | A1 | 7/2010 | Braido et al. |
| 2010/0168844 | A1 | 7/2010 | Toomes et al. |
| 2010/0185277 | A1 | 7/2010 | Braido et al. |
| 2010/0191326 | A1 | 7/2010 | Alkhatib |
| 2010/0204781 | A1 | 8/2010 | Alkhatib |
| 2010/0204785 | A1 | 8/2010 | Alkhatib |
| 2010/0217382 | A1 | 8/2010 | Chau et al. |
| 2010/0234940 | A1 | 9/2010 | Dolan |
| 2010/0249911 | A1 | 9/2010 | Alkhatib |
| 2010/0249923 | A1 | 9/2010 | Alkhatib et al. |
| 2010/0286768 | A1 | 11/2010 | Alkhatib |
| 2010/0298931 | A1 | 11/2010 | Quadri et al. |
| 2011/0029072 | A1 | 2/2011 | Gabbay |
| 2011/0054466 | A1 | 3/2011 | Rothstein et al. |
| 2011/0066233 | A1 | 3/2011 | Thornton et al. |
| 2011/0098800 | A1 | 4/2011 | Braido et al. |
| 2011/0098802 | A1 | 4/2011 | Braido et al. |
| 2011/0137397 | A1 | 6/2011 | Chau et al. |
| 2011/0172765 | A1 | 7/2011 | Nguyen et al. |
| 2011/0208283 | A1 | 8/2011 | Rust |
| 2011/0264206 | A1 | 10/2011 | Tabor |
| 2012/0035722 | A1 | 2/2012 | Tuval |
| 2012/0078347 | A1 | 3/2012 | Braido et al. |
| 2012/0078358 | A1 | 3/2012 | Vidlund et al. |
| 2012/0101572 | A1 | 4/2012 | Kovalsky et al. |
| 2012/0123529 | A1 | 5/2012 | Levi et al. |
| 2012/0303116 | A1 | 11/2012 | Gorman, III et al. |
| 2013/0274873 | A1 | 10/2013 | Delaloye et al. |
| 2014/0121763 | A1 | 5/2014 | Duffy et al. |
| 2014/0155997 | A1 | 6/2014 | Braido |
| 2014/0214159 | A1 | 7/2014 | Vidlund et al. |
| 2014/0228946 | A1 | 8/2014 | Chau et al. |
| 2014/0303719 | A1 | 10/2014 | Cox et al. |
| 2014/0324164 | A1 | 10/2014 | Gross et al. |
| 2014/0343671 | A1 | 11/2014 | Yohanan et al. |
| 2014/0350668 | A1 | 11/2014 | Delaloye et al. |
| 2014/0350669 | A1 | 11/2014 | Gillespie et al. |

FOREIGN PATENT DOCUMENTS

| | | | |
|---|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 2537487 A1 | 12/2012 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

(56) References Cited

OTHER PUBLICATIONS

Quaden et al., "Percutaneous aortic valve replacement: resection before implantation", pp. 836-840, European J. of Cardio-thoracic Surgery, 27 (2005).
Ruiz, Carlos, Overview of PRE-CE Mark Transcatheter Aortic Valve Technologies, Euro PCR, dated May 25, 2010.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,243, filed Sep. 20, 2010.
U.S. Appl. No. 29/375,260, filed Sep. 20, 2010.
78. Heart repairs without surgery. Minimally invasive procedures aim to correct valve leakage. PubMed ID 15586429.
Buellesfeld et al., Treatment of paravalvular leaks through inverventional techniques; Department of Cardiology, Ben University Hospital 2011.
De Cicco, Giuseppe, et al. "Aortic valve periprosthetic leakage: anatomic observations and surgical results." The Annals of thoracic surgery 79.5 (2005): 1480-1485.
Gössl, Mario, and Charanjit S. Rihal. "Percutaneous treatment of aortic and mitral valve paravalvular regurgitation." Current cardiology reports 15.8 (2013): 1-8.
Muñoz, Daniel Rodriguez, Carla Lázaro Rivera, and José Luis Zamorano Gómez. "Guidance of treatment of perivalvular prosthetic leaks." Current cardiology reports 16.1 (2014): 1-6.
Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets In Vitro by Q-Switched 2?μm Microsecond Laser Radiation. Journal of Cardiac Surgery, 30: 157-162. doi: 10.1111/jocs.12481.
Swiatkiewicz, Iwona, et al. "Percutaneous closure of mitral perivalvular leak." Kardiologia polska 67.7 (2009): 762.
Transcatheter Umbrella Closure of Valvular and Paravalvular Leaks, Hourihan et al., Journal of the American College of Cardiology, vol. 20, No. 6, pp. 1371-1377, (1992).
Kit Definition, Collins English Dictionary.

* cited by examiner

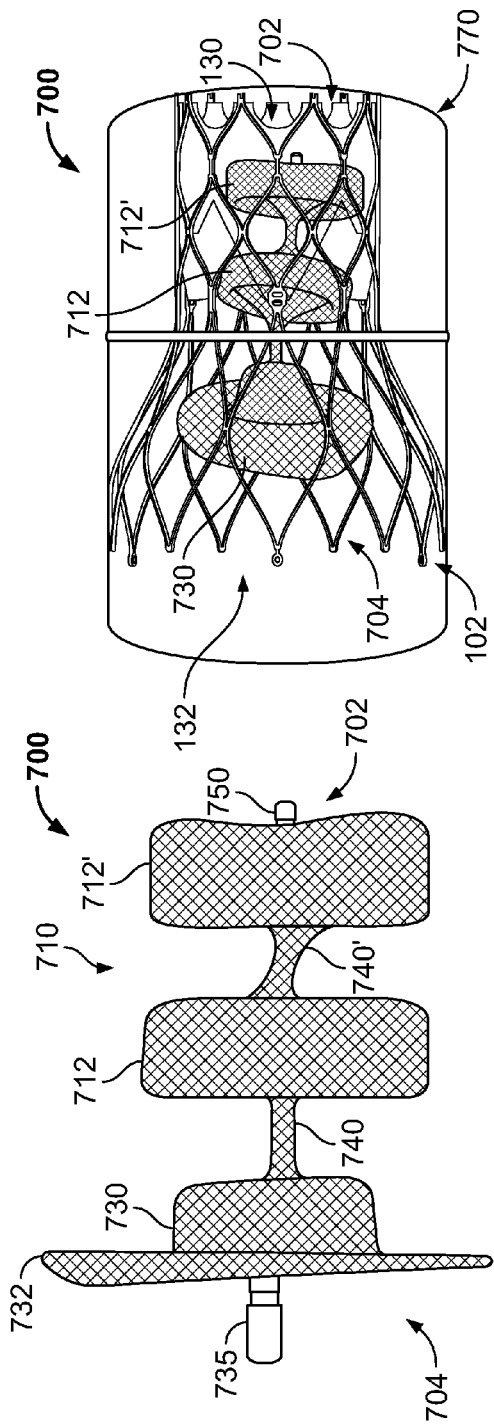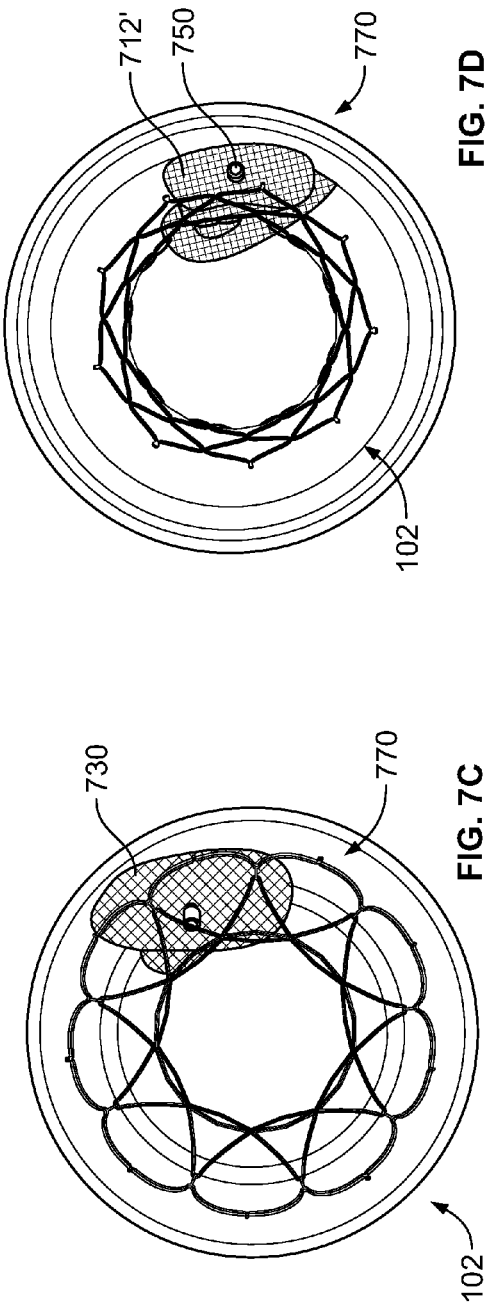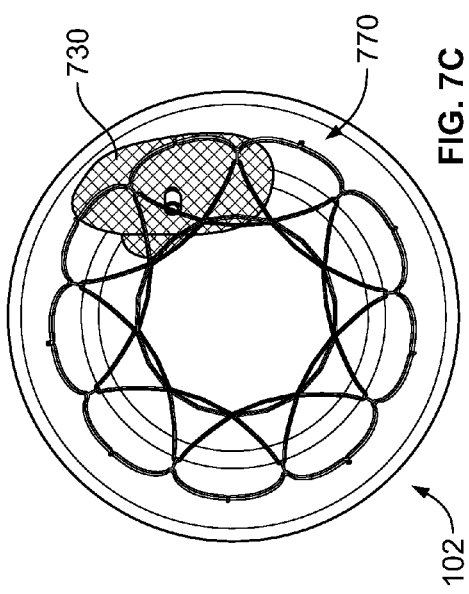

… (1)

PARAVALVULAR LEAK OCCLUSION DEVICE FOR SELF-EXPANDING HEART VALVES

BACKGROUND OF THE INVENTION

The present disclosure relates in general to heart valve replacement and, in particular, to collapsible prosthetic heart valves. More particularly, the present disclosure relates to devices and methods for positioning and sealing of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, an occluder device for occluding a gap between a medical device and adjacent body tissue includes an expandable body having a first end and a second end, a fastener coupled to the first end of the body, and an expandable disk coupled to the second end of the body.

In some embodiments, a method for occluding a gap between a prosthetic heart valve and adjacent body tissue includes delivering an occluder into the interior of the heart valve, the occluder having (i) an expandable body, (ii) a fastener coupled to one end of the body, and (iii) an expandable disk coupled to another end of the body. The occluder is advanced through a cell of the heart valve to the outside of the heart valve. The fastener is coupled to one end of the prosthetic heart valve and the expandable disk is coupled to the prosthetic heart valve at a position spaced from the one end.

BRIEF DESCRIPTION OF THE DRAWINGS

Various embodiments of the present disclosure are described herein with reference to the drawings, wherein:

FIG. 7A is a side view of a conformable occluder in accordance with another embodiment of the present disclosure; and FIGS. 7B-D are side, top and bottom views showing the use of the conformable occluder of FIG. 7A in vitro.

DETAILED DESCRIPTION

Figure 1:
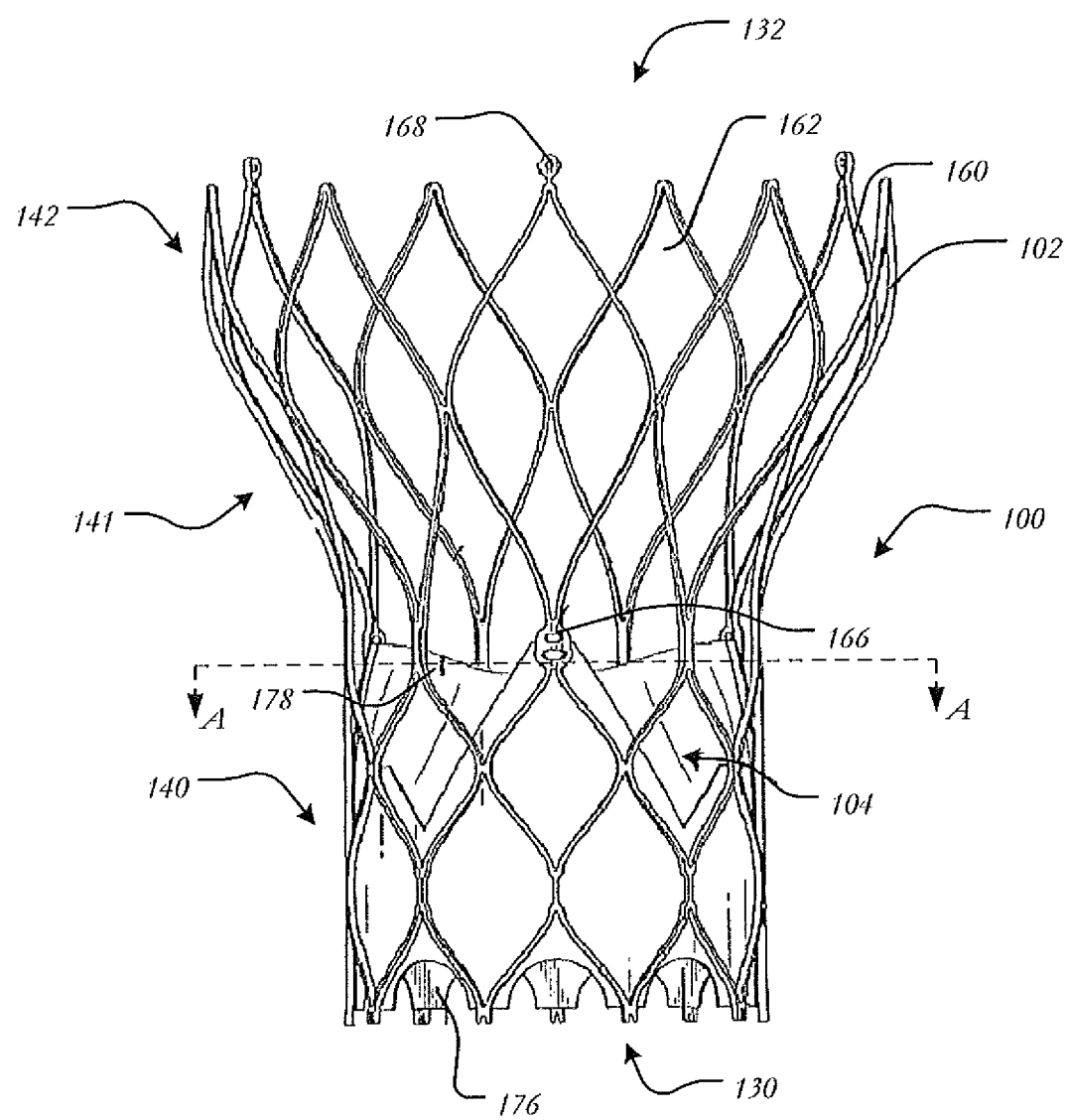
FIG. 1 is a side elevational view of a conventional prosthetic heart valve.

Despite the various improvements that have been made to the collapsible prosthetic heart valve delivery process, conventional devices suffer from some shortcomings. For example, with conventional self expanding valves, clinical success of the valve is dependent on accurate deployment and anchoring. Inaccurate deployment and anchoring of the valve increases risks, such as those associated with valve migration, which may cause severe complications and possibly death due to the obstruction of the left ventricular outflow tract. Inaccurate deployment and anchoring may also result in the leakage of blood between the implanted heart valve and the native valve annulus, commonly referred to as paravalvular leakage. This leakage enables blood flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations between patients may require removal of a fully deployed heart valve from the patient if it appears that the valve is not functioning properly. Removing a fully deployed heart valve increases the length of the procedure and increases the risk of infection and/or damage to heart tissue. Thus, methods and devices are desirable that would reduce the likelihood of removal. Methods and devices are also desirable that would reduce the likelihood of valve leakage due to gaps formed between the implanted heart valve and patient tissue known as paravalvular leaks.

There therefore is a need for further improvements to the devices, systems, and methods for transcatheter delivery and positioning of collapsible prosthetic heart valves. Specifically, there is a need for further improvements to the devices, systems, and methods for accurately implanting a prosthetic heart valve. Among other advantages, the present disclosure may address one or more of these needs.

Various embodiments of the present invention will now be described with reference to the appended drawings. It is to be appreciated that these drawings depict only some embodiments of the invention and are therefore not to be considered limiting of its scope.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user.

The leak occluders of the present invention may be used in connection with collapsible prosthetic heart valves. FIG. 1 shows one such collapsible stent-supported prosthetic heart valve 100 including a stent 102 and a valve assembly 104 as known in the art. The prosthetic heart valve 100 is designed to replace a native tricuspid valve of a patient, such as a native aortic valve. It should be noted that while the inventions herein are described predominately in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 will be described in more detail with reference to FIG. 1. Prosthetic heart valve 100 includes expandable stent 102 which may be formed from, for example, a shape memory material, such as the nickel-titanium alloy known as "Nitinol" or other suitable metals. and in particular, from those materials that are capable of self-expansion. Stent 102 extends from proximal or annulus end 130 to a distal or aortic end 132, and includes annulus section 140 adjacent proximal end 130, transition section 141 and aortic section 142 adjacent distal end 132. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may also include a plurality of commissure features 166 for attaching the commissure between two adjacent leaflets to stent 102. As can be seen in FIG. 1, commissure features 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to the stent.

Stent 102 may include one or more retaining elements 168 at distal end 132 thereof, retaining elements 168 being sized and shaped to cooperate with female retaining structures (not shown) provided on the deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably positioned in annulus section 140 of the stent 102 and secured to the stent. Valve assembly 104 includes cuff 176 and a plurality of leaflets 178 which collectively function as a one-way valve by coapting with one another. As a prosthetic aortic valve, valve 100 has three leaflets 178, as well as three commissure features 166. However, it will be appreciated that other prosthetic heart valves with which the leak occluders of the present invention may be used may have a greater or lesser number of leaflets 178 and commissure features 166.

Although cuff 176 is shown in FIG. 1 as being disposed on the lumenal or inner surface of annulus section 140, it is contemplated that cuff 176 may be disposed on the ablumenal or outer surface of annulus section 140 or may cover all or part of either or both of the lumenal and ablumenal surfaces. Both cuff 176 and leaflets 178 may be wholly or partly formed of any suitable biological material or polymer such as, for example, polytetrafluoroethylene (PTFE).

Prosthetic heart valve 100 may be used to replace a native aortic valve, a surgical heart valve or a heart valve that has undergone a surgical procedure. The prosthetic heart valve may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Problems may be encountered when implanting prosthetic heart valve 100. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency cannot be treated well, if at all, with the current collapsible valve designs.

The reliance on unevenly calcified leaflets for proper valve placement and seating could lead to several problems, such as paravalvular (also known as perivalvular) leakage (PV leak), which can have severe adverse clinical outcomes. To reduce these adverse events, the optimal valve would anchor adequately and seal without the need for excessive radial force that could harm nearby anatomy and physiology.

Figure 2:
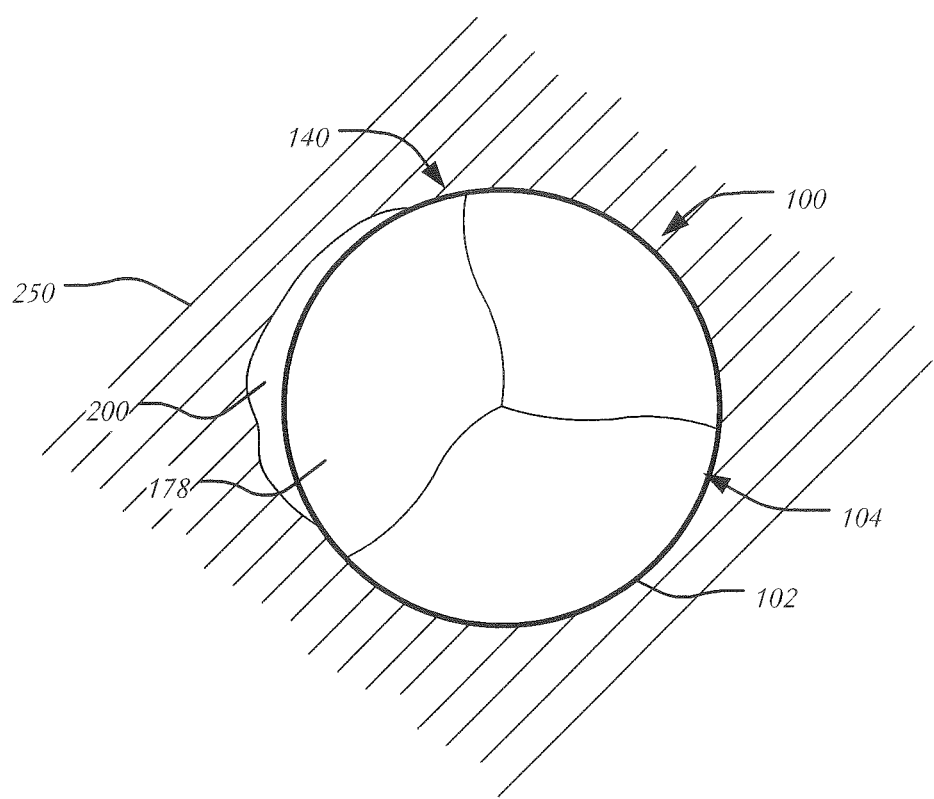
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, annulus section 140 of the stent 102 has a substantially circular cross-section which is disposed within the non-circular native valve annulus 250. At certain locations around the perimeter of heart valve 100, crescent-shaped gaps 200 form between heart valve 100 and native valve annulus 250. Blood flowing through these gaps and past valve assembly 104 of prosthetic heart valve 100 can cause regurgitation and other inefficiencies which reduce cardiac performance. Such improper fitment may be due to suboptimal native valve annulus geometry due, for example, to calcification of native valve annulus 250 or to unresected native leaflets.

Figure 3A:
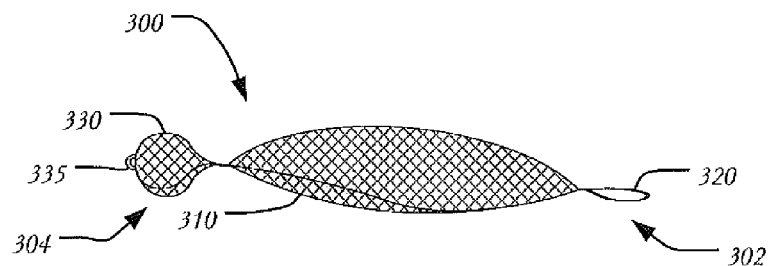
FIG. 3A is a side view of a conformable occluder in accordance with one embodiment of the present disclosure.
Figure 3B:
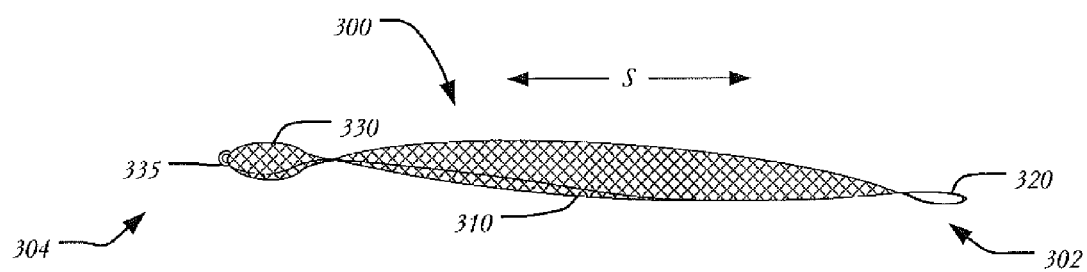
FIG. 3B is a side view of the conformable occluder of FIG. 3A after it has been stretched longitudinally.

FIGS. 3A and 3B illustrate one embodiment of conformable occluder 300 intended to fill irregularities between heart valve 100 and native valve annulus 250 shown in FIG. 2. As will be described in more detail below, conformable occluder 300 allows for superior sealing between the perimeter of heart valve 100 and native valve annulus 250 while affording a low radial outward force. FIG. 3A, shows conformable occluder 300 in a relaxed and expanded configuration while FIG. 3B shows conformable occluder 300 in a stretched and partially elongated configuration. Conformable occluder 300 has a leading end 302 and a trailing end 304, and may generally include body 310, fastener 320, and disk 330.

Body 310 may be a metallic structure that may be longitudinally stretched in the direction of arrows S from a relaxed condition shown in FIG. 3A to a stretched condition shown in FIG. 3B. In the relaxed condition, body 310 may have a cross-section that is greater in size than it is in the stretched condition. Thus, body 310 of conformable occluder 300 may be flexible and capable of contracting in the radial direction when a force is applied thereto to conform to the shape of the annulus in which it will be implanted. Moreover, the ability of body 310 to longitudinally stretch in the direction of arrow S will allow the occluder to be delivered through a small diameter catheter and to be secured between two attachment points as will be seen below with reference to FIGS. 4A-4F.

Occluder 300 may be formed from a tubular section of braided fabric comprising a plurality of braided strands. The strands forming the braid may have a predetermined relative orientation with respect to one another (e.g., a helical braid). The ends of the strands may be located at leading end 302 and trailing end 304 and affixed to prevent unraveling by any suitable means such as solder, braze, weld, coat, glue, clamp, tie, or clamp. Moreover, occluder 300 may comprise a plurality of layers of braided fabric and/or other occluding material (e.g. see filler 345 in FIG. 3C) such that occluder 300 is capable of at least partially inhibiting blood flow therethrough in order to facilitate the formation of thrombus and epithelialization.

Occluder 300 may be formed, for example, of a braided fabric mesh of a shape-memory material, of a super-elastic material, of a bio-compatible polymer, or of another material that is capable of collapsing and expanding. In the embodiments depicted in FIGS. 3A-3C, occluder 300 comprises a braided metal fabric that is both resilient and capable of heat treatment to substantially set a desired preset shape (e.g. the relaxed configuration shown in FIG. 3A). One class of materials which meets these qualifications is shape memory alloys. One example of a shape memory alloy is Nitinol. It is also understood occluder 300 may comprise various materials other than Nitinol that have elastic and/or memory properties, such as spring stainless steel, trade named alloys such as Elgiloy®, Hastelloy®, CoCrNi alloys (e.g., trade name Phynox), MP35N®, CoCrMo alloys, or a mixture of metal and polymer fibers. Depending on the individual material selected, strand diameter, number of strands, and pitch may be altered to achieve the desired properties of occluder 300.

As further described below, body 310 may be collapsed during delivery into the patient and re-expanded after delivery to occlude gaps between a prosthetic heart valve and the native valve annulus to one side of the valve. While body 310 is shown in FIG. 3A as having an elliptical longitudinal cross-section in the expanded condition, it will be understood that the body may be constructed with various shapes and/or sizes. For example, body 310 may have a circular, oval, polygonal, square, diamond, triangular or other shape in longitudinal cross-section when expanded. Body 310 may also include two or more segments. Additionally, body 310 may be formed of multiple layers of braid to decrease occlusion time.

Body 310 may be connected to fastener 320 at leading end 302 of conformable occluder 300. Fastener 320 may be formed of a suture, polymeric fiber, metallic filament, such as a flexible stranded stainless steel cable or loop of nitinol wire, or other suitable material, and may be configured to secure conformable occluder 300 to prosthetic heart valve 100 as will be described in greater detail below. Though fastener 320 is shown in FIG. 3A as a loop, it will be understood that a simple hook, clasp or other similar structure capable of grasping, clipping, or hooking conformable occluder 300 to strut 160 of prosthetic heart valve 100 may be used.

Body 310 may further be coupled to disk 330 at trailing end 304 of conformable occluder 300. In the depicted embodiment, body 310 is coupled to disk 330 by a small diameter waist. Disk 330 may be an ovular or spherical body sized to couple conformable occluder 300 to a cell of a prosthetic heart valve. Specifically, disk 330 may be sized larger than cell 162 of stent 102 such that it is incapable of passing through the cell (see FIG. 1). Disk 330 may be formed of the same material as body 310 or from a different material. For example, disk 330 may be formed of a braided nitinol mesh or other shape-memory mesh. It is also contemplated that disk 330 may be constructed from a bio-compatible polymer material. Disk 330 may include a lip having a greater cross-sectional dimension than disk 330. Female component 335 connected to disk 330 at trailing edge 335 may be used to couple conformable occluder 300 to a delivery device to position and deliver conformable occluder 300. Female component 335 may include an internally threaded screw attachment, a ring, or any other suitable means for coupling with a delivery device.

Figure 3C:
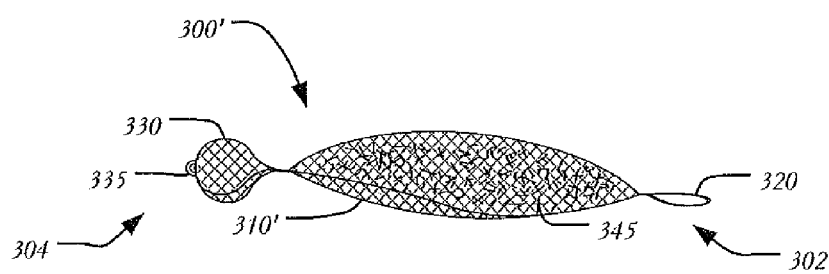
FIG. 3C is a side view of a conformable occluder having a filler in accordance with another embodiment of the present invention.

In one example, as shown in FIG. 3C, body 310' may be hollow and may be at least partially filled with filler 345 of a fabric or fibers of materials that are intertwined within the mesh of conformable occluder 300' to assist with sealing, occlusion and healing. For example, body 310' may include filler 345 of polyester threads or polyester fabric, as well as any suitable fiber material to increase density and/or promote tissue growth. Filler 345 may also be in the form of a foam material, such as a closed cell sponge. The density of body 310' may be such that it impedes the flow of blood through it. Inclusion of filler 345 in body 310' may speed occlusion time for conformable occluder 300'.

Figure 3D:
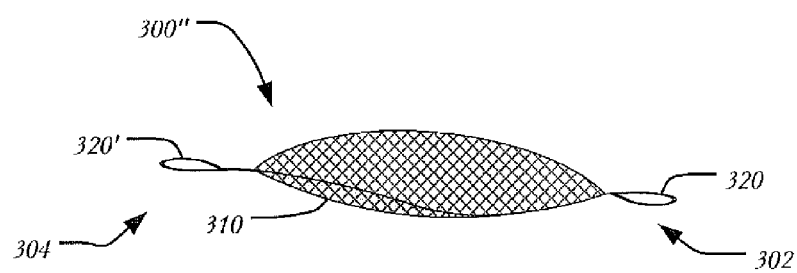
FIG. 3D is a side view of a conformable occluder having two fasteners in accordance with another embodiment of the present invention.

In an alternative embodiment, shown in FIG. 3D, occluder 300" has leading end 302 and trailing end 304, and may generally include body 310 extending entirely from leading end 302 to the trailing end 304. As seen in FIG. 3D, occluder 300" includes first fastener 320 at leading end 302. Instead of a disk on the opposite end (see disk 335 in FIGS. 3A-3C), occluder 300" includes second fastener 320' disposed near trailing end 304. In this embodiment, occluder 300" may be coupled to select struts 160 of stent 102 via first and second fasteners 320,320' without the need for disk 335.

Figure 4A:
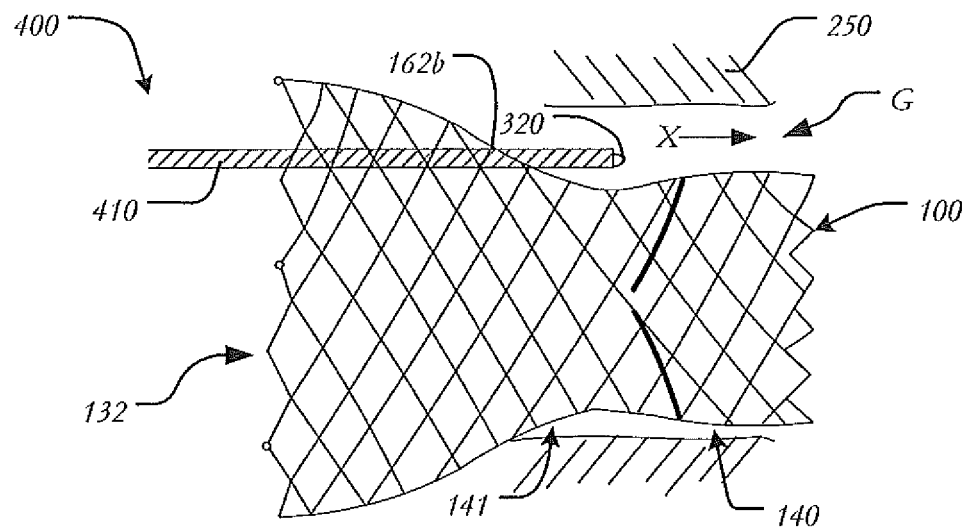
FIGS. 4A-F illustrate the steps used to insert a conformable occluder to seal a prosthetic heart valve within a native valve annulus.

FIGS. 4A-F illustrate the steps used to insert conformable occluder 300 (or conformable occluder 300' or conformable occluder 300") to seal heart valve 100 within native valve annulus 250. As seen in FIG. 4A, heart valve 100 has been implanted in a patient with annulus portion 140 thereof positioned in native valve annulus 250. Gap G may be formed between heart valve 100 and native valve annulus 250 to one side of heart valve 100.

Figure 4B:
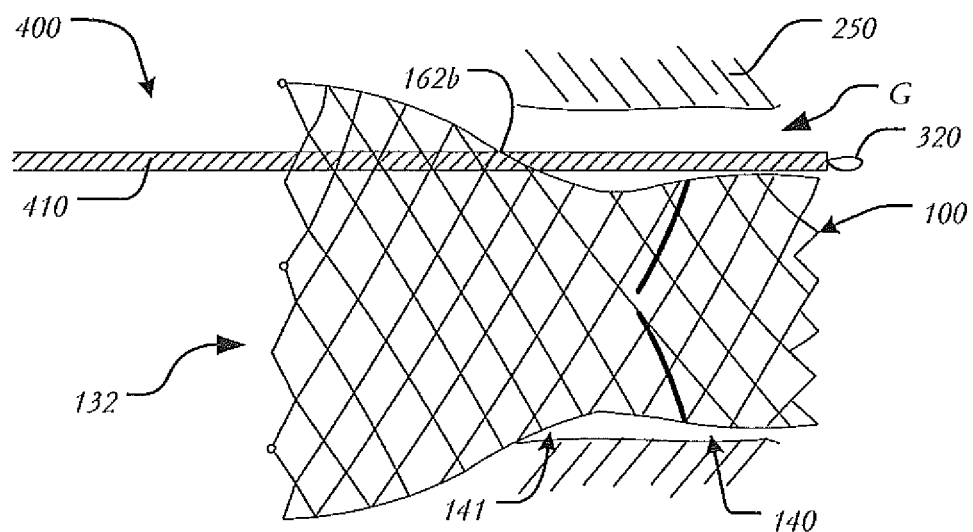

As an initial step to seal gap G, conformable occluder 300 may be disposed within delivery system 400 (FIG. 4A) in a collapsed condition, such as the stretched or elongated configuration shown in FIG. 3B. Delivery system 400 may include outer sheath 410 and inner wire 420 having male component 425. Male component 425 may include a conventional screw attachment, a terminal hook or other suitable structure for mating with female component 335. Male component 425 is configured to couple with female component 335 of conformable occluder 300 (elements shown uncoupled in FIG. 4F). Outer sheath 410 is slidable relative to inner wire 420. Delivery system 400 may be inserted into the patient and advanced toward the implanted heart valve 100 in the direction of arrow X. As it reaches heart valve 100, delivery system 400 may be advanced into the heart valve 100 at aortic end 132 and out therefrom through cell 162b in transition section 141 (shown in FIG. 4A). Delivery system 400 may then be further advanced through gap G toward annulus end 140 of implanted heart valve 100, as shown in FIG. 4B. If heart valve 100 or delivery system 400 includes echogenic materials, such materials may be used to guide delivery system 400 to the appropriate position using the assistance of three-dimensional echocaradiography to visualize heart valve 100 within the patient.

Figure 4C:
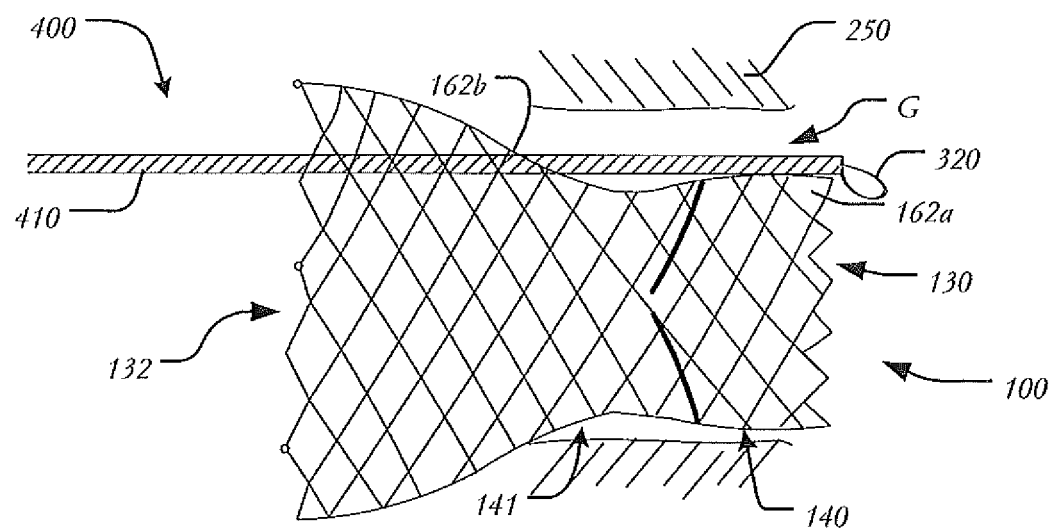
Figure 4D:
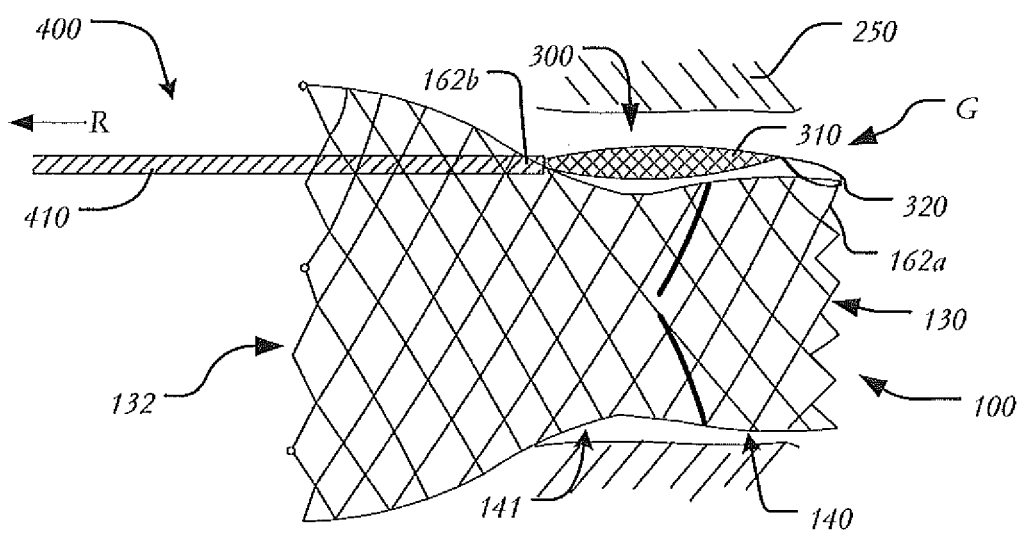

Once delivery system 400 has reached the desired site of sealing (e.g. gap G) as shown in FIG. 4C, outer sheath 410 may be retracted slightly in the direction of arrow R (toward the trailing end of delivery system 400) to expose fastener 320 (shown in FIG. 4D). Conformable occluder 300 remains coupled to inner wire 420 at this stage and trailing edge 304 of occluder 300 remains housed by delivery system 400.

Figure 4E:
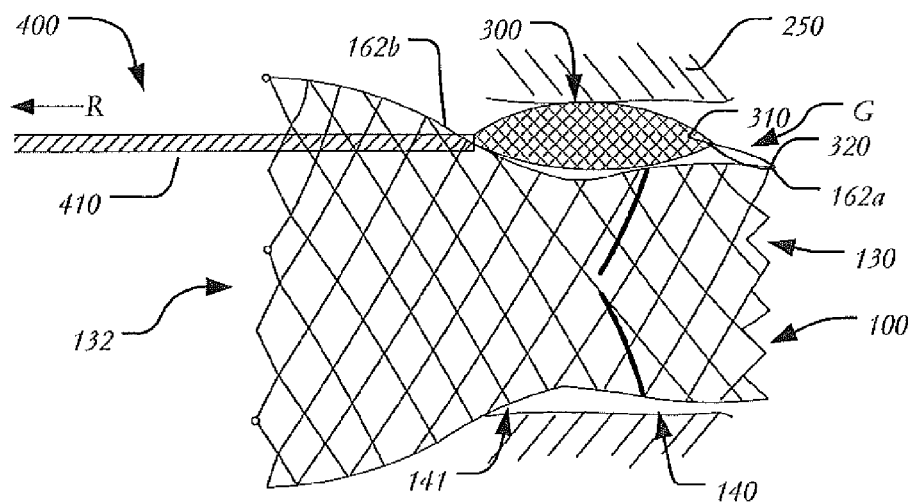
Figure 4F:
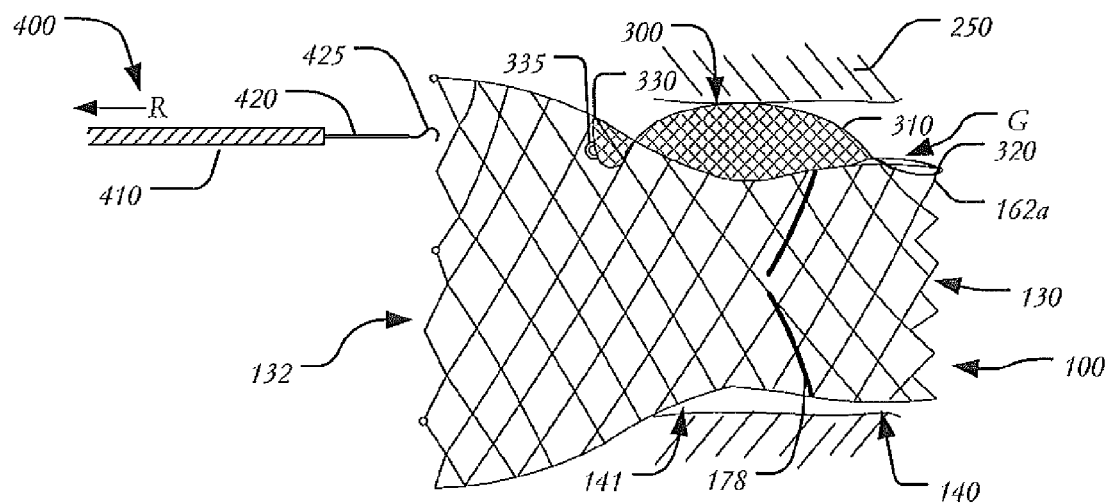

Delivery system 400 may be manipulated by gently twisting and/or tilting delivery system 400 to position fastener 320 over the apex of cell 162a at annulus end 130 of heart valve 100. Once fastener 320 has latched onto or been looped around apex of cell 162a, outer sheath 410 may be further retracted in the direction of arrow R to expose body 310 of conformable occluder 300. As outer sheath 410 is further retracted, more of occluder body 310 is exposed and occluder 300 expands within the gap G between heart valve 100 and native valve annulus 250 (FIGS. 4D and 4E). As seen in FIGS. 4D-4F, body 310 is positioned parallel to annulus section 140 and transition section 141. In this intermediate stage of deployment, body 310 has expanded to its relaxed state and contacted the walls of native valve annulus 250, and substantially fills gap G.

Outer sheath 410 may then be fully retracted to expose disk 330 and allow it to expand near cell 162b. In the depicted embodiment, disk 330 is located on the interior of heart valve 100, although other in other embodiments, disk 330 is located on the exterior of heart valve 100. In either instance, disk 330 is spaced away from valve assembly 104 so as not to impede normal leaflet 178 function. Disk 330 then expands to a size small enough for disk 300 to project partially out of or into cell 162b, but remains too large to pass through that cell. The interference of disk 330 with cell 162b creates a second attachment region for conformable occluder 300. Thus, conformable occluder 300 is stretched between the two attachment regions—the interference between disk 330 and cell 162b and the connection between fastener 320 and cell 162a. Fastener 320 prevents occluder 300 from migrating into the aorta, while disc 330 prevents occluder 300 from migrating back into the heart. Alternatively, in embodiments having two fasteners instead of disk 330 such as that shown in FIG. 3D, first fastener 320 may be coupled to the apex of cell 162a, while second fastener 320' may be likewise coupled over the apex of a cell at the aortic end 132 of stent 100.

Male component 425 may be disconnected from female component 335 by manipulating (e.g., rotating) wire 420. Alternatively, inner wire 420 may comprise a suture tied to female component 335, and the suture may be simply cut to release conformable occluder 300 from delivery system 400. In another example, male and female components may be threaded and delivery system 400 may be twisted relative to occluder 300 to decouple the two from one another. Accordingly, many mating solutions between delivery system 400 and occluder 300 would serve the intended purpose for deployment of occluder 300. FIG. 4F illustrates heart valve 100 in its fully expanded state with conformable occluder 300 fully filling the gap G between heart valve 100 and native valve annulus 250. Delivery system 400 may then be withdrawn in the direction of arrow R and removed from the patient, leaving conformable occluder 300 in place to seal valve 100 within native valve annulus 250.

Figure 5:
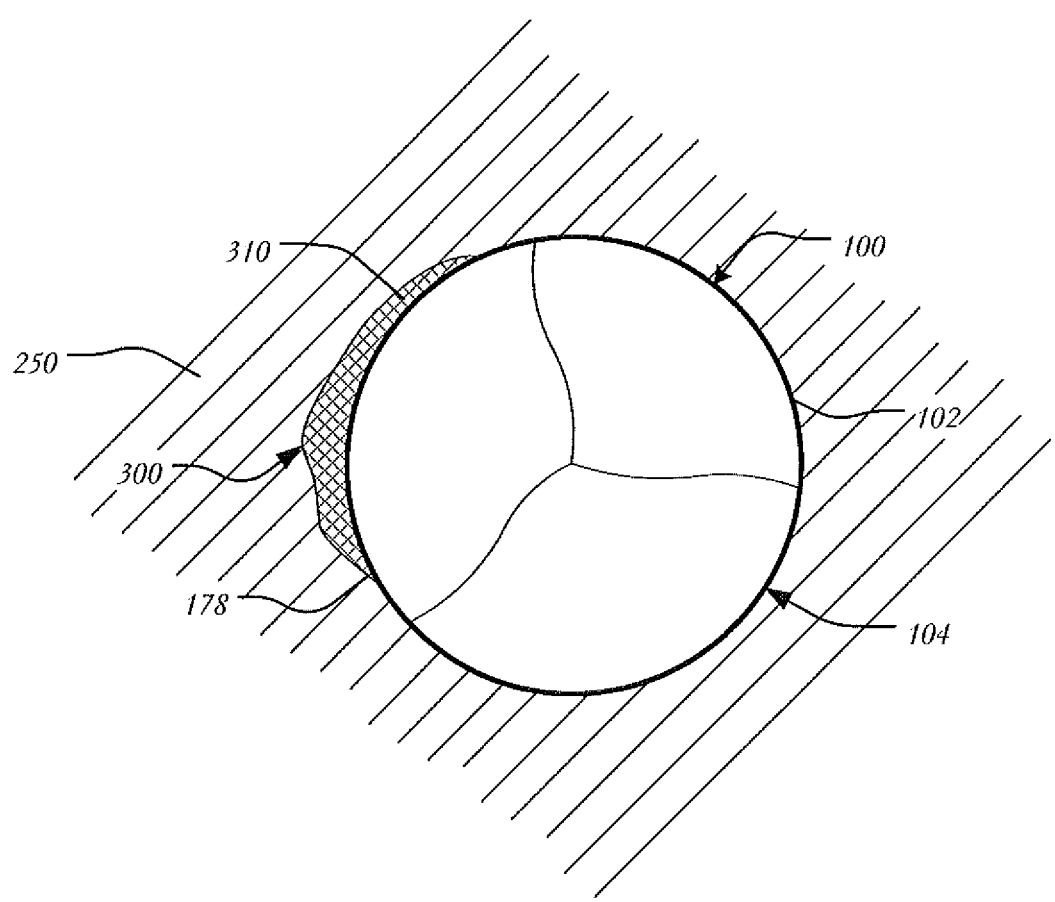
FIG. 5 is a highly schematic cross-sectional view showing a prosthetic heart valve disposed within a native valve annulus along with a conformable occluder in its fully expanded state.

FIG. 5 is a highly schematic cross-sectional view showing conformable occluder 300 in its relaxed state with body 310 fully radially expanded to fill crescent-shaped gap 200 shown in FIG. 2. The mesh of conformable occluder 300 may be capable of promoting tissue growth between heart valve 100 and native valve annulus 250. For example, conformable occluder 300 may be treated with a biological or chemical agent to promote tissue growth on the conformable occluder, further sealing the heart valve within the native valve annulus. Alternatively, conformable occluder 300 may be sufficiently dense through the use of polyester fibers or polyester fabric to adequately seal the heart valve without the need for major tissue growth throughout gap G. Occluder 300 may also be double-layered and/or may include tighter braiding to more quickly occlude the space between heart valve 100 and native valve annulus 250. When conformable occluder 300 is functioning properly, heart valve 100 will be adequately sealed within native valve annulus 250 so that blood flows through valve assembly 104 and passing through leaflets 108, while limiting or at least reducing blood flow through any gaps formed between heart valve 100 and native valve annulus 250.

Figure 6B:
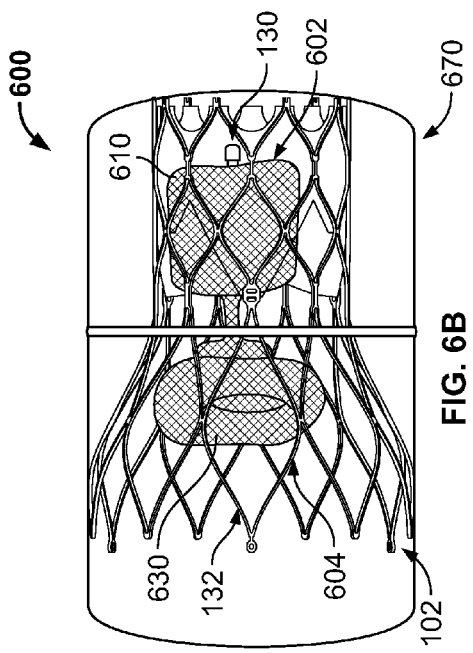
FIGS. 6B-D are side, top and bottom views showing the use of the conformable occluder of FIG. 6A in vitro.
Figure 6D:
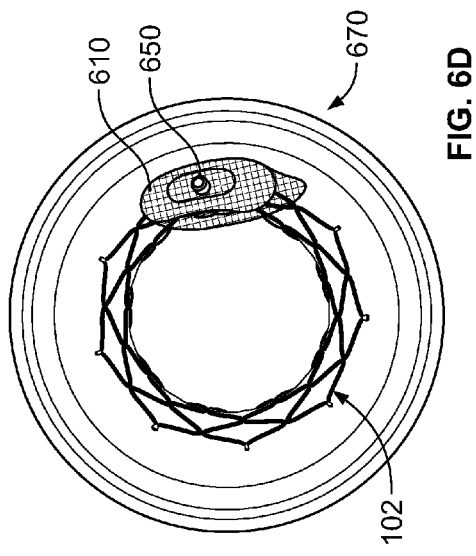
Figure 6A:
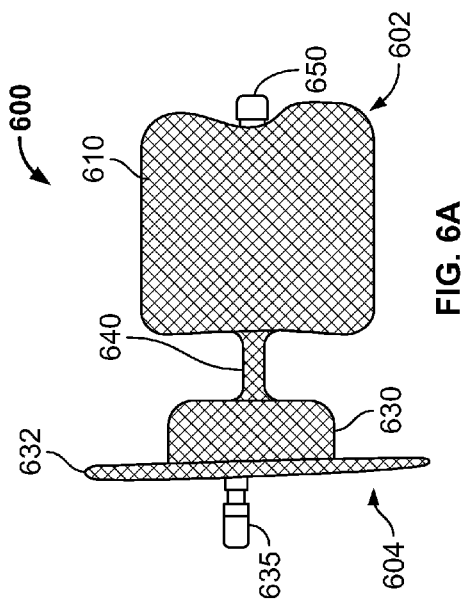
FIG. 6A is a side view of a conformable occluder in accordance with another embodiment of the present disclosure.

FIG. 6A illustrates another embodiment of conformable occluder 600. Conformable occluder 600 extends between leading end 602 and trailing end 604, and may generally include a tubular body 610 and disk 630. Disk 630 includes an enlarged outer rim 632 and is coupled to connector 635 for mating with a delivery system (not shown). As seen in FIG. 6A, reduced diameter neck portion 640 connects body 610 to disk 630. A fastener (not shown) may be attached to joint 650 at leading end 602 to connect occluder 600 to an apex of a cell 162 as described above with reference to FIGS. 4A-4F.

Figure 6C:
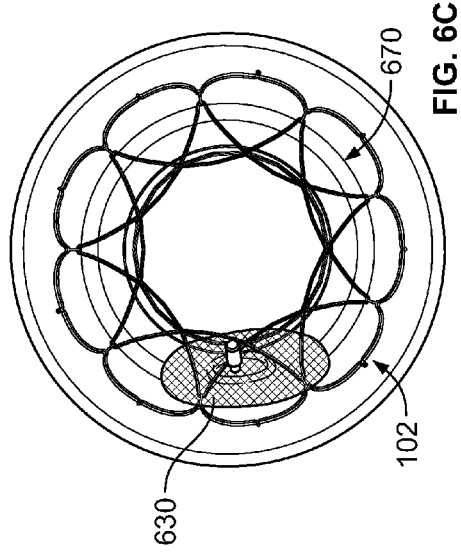

FIGS. 6B-D are side, top and bottom end views illustrating the use of occluder 600. Specifically, FIG. 6B shows a side view of the system while FIG. 6C illustrates a top view (e.g., as seen from aortic end 132 of stent 102) and FIG. 6D illustrates a bottom view (e.g., as seen from annulus end 130 of stent 102). In these figures, container 670 approximates the native valve annulus and stent 102 is disposed therein to simulate a prosthetic heart valve 100. A valve assembly is not shown attached to the stent 102 for the sake of clarity. As seen in FIGS. 6B-D occluder 600 is coupled to stent 102 and shown to fill a gap between stent 102 and the native valve annulus, approximated by the walls of container 670. Specifically, disk 630 is shown disposed within the interior of stent 102 (FIG. 6C) and body 610 is disposed outside of stent 102

(FIG. 6D). Though a fastener is not shown, it will be understood that a fastener may attach to joint 650 and couple leading end 602 of occluder 600 to an apex of a cell at annulus end 130 of stent 102. Occluder 600 may be delivered and positioned in a manner similar to that described above with reference to FIGS. 4A-F.

FIG. 7A illustrates another embodiment of conformable occluder 700. Conformable occluder 700 extends between leading end 702 and trailing end 704, and may generally include a body 710 formed of two body segments 712,712', and disk 730. Though occluder 700 is shown having two segments 712,712' it will be understood that three or more segments may be employed in constructing occluder 700. In some instances, it may be helpful to use multiples segments 712,712' as opposed to a single unitary body to improve occlusion. For example, first segment 712 may expand to a small radius, while a second segment 712' may expand to a larger radius to accommodate a non-uniform native valve annulus and fill multiple gaps at varying longitudinal extents.

Disk 730 includes an enlarged outer rim 732 and is coupled to connector 735 for mating with a delivery system (not shown). As seen in FIG. 7A, two reduced diameter neck portions 740,740' connect body disk 730 to first segment 712 and first segment 712 to second segment 712', respectively. A fastener (not shown) may be attached to joint 750 at leading end 702 to connect occluder 700 to an apex of a cell 162 as described above with reference to FIGS. 4A-4F.

FIGS. 7B-D are side, top and bottom end views illustrating the use of occluder 700 within an approximating container 770 as described above with reference to FIGS. 6B-6D. As seen in FIGS. 7B-D occluder 700 is coupled to stent 102 and shown to fill a gap between stent 102 and the native valve annulus, approximated by the walls of container 770. Specifically, disk 730 is shown disposed within the interior of stent 102 (FIG. 6C) and segments 712,712' are disposed outside of stent 102 (FIG. 6D). Though a fastener is not shown, it will be understood that a fastener may attach to joint 750 to couple leading end 702 of occluder 700 to an apex of a cell at annulus end 130 of stent 102. Occluder 700 may be delivered and positioned in a manner similar to that described above with reference to FIGS. 4A-F.

While the inventions herein have been described for use in connection with heart valve stents having a particular shape, the stent could have different shapes, such as a flared or conical annulus section, a less-bulbous aortic section, and the like, and a differently shaped transition section. Additionally, though conformable occluder 300 has been described in connection with expandable transcatheter aortic valve replacement, it may also be used in connection with surgical valves, sutureless valves and other devices in which it is desirable to create a seal between the periphery of the device and the adjacent body tissue. Additionally, though the deployment of occluder 300 has been described using delivery system 400 that deploys fastener 320 first, followed by body 310 and finally disk 330, it will be understood that, through a different delivery approach, such as, for example, a transapical route, disk 330 may be deployed first, followed by body 310 and then fastener 320.

It will also be understood that while the preceding disclosure has illustrated the use of a single occluder to fill gaps to one side of a prosthetic heart valve, it will be understood that multiple occluders may be deployed around the perimeter of a heart valve. Such occluders may be delivered successively to each gap formed between the prosthetic heart valve and the native valve annulus. Conversely, multiple occluders may be delivered simultaneously using a large single outer sheath having two or more male components or other connectors. Additionally, multiple occluders may be simultaneously deployed by using multiple delivery systems each having a male component or other connector.

Moreover, although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

For examples, the occluder may be deployed for use with a prosthetic heart valve having a collapsible and expandable stent forming cells, and a valve assembly disposed in the stent for controlling the flow of blood through the stent. The disk is expandable from a collapsed configuration to a relaxed configuration, the disk in the relaxed configuration having a size larger than the size of at least some of the cells of the stent. The stent may include a plurality of struts and the fastener is coupleable to at least one of the plurality of the struts. The body may include at least one of a metallic mesh or a shape-memory material. The body may have an elliptical longitudinal cross-section. The body may include a metal mesh and polyester fiber intertwined with the metal mesh to increase the density of the body. The fastener may include a loop for coupling to the medical device. The disk may include at least one of a metallic mesh or a shape-memory material.

The device may also include a female component or other connected attached to the disk for coupling to a delivery device. The body may include an agent for promoting tissue growth. A system for occluding a gap between a medical device and adjacent body tissue may include the occluder and a delivery system including an outer sheath, an inner wire disposed within and translatable with respect to the outer sheath, and a male component or other connector attached to the inner wire, the male component or other connector being configured to couple the inner wire to the expandable disk of the occluder. The outer sheath may be adapted to house the occluder in a contracted configuration, the medical device is a prosthetic heart valve having a collapsible and expandable stent forming cells and a valve assembly disposed in the stent for controlling the flow of blood through the stent, and the outer sheath is sized to pass through a cell of the expandable stent.

In the methods described above, the fastener may be a loop and the step of coupling the fastener may include positioning the loop around an apex of a cell at the one end of the prosthetic heart valve. The body may have a substantially elliptical longitudinal cross-section in an expanded condition.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A system for replacing native valve function, the system comprising:
    a prosthetic heart valve having a collapsible and expandable stent forming cells, the stent having a plurality of sections including an annulus section, a transition section and an aortic section, and a valve assembly disposed in the stent; and
    an occluder device comprising an expandable body having a first end and a second end, a fastener coupled to the first end of the body and to a selected strut of the stent at a first position on the annulus section of the stent, and an expandable disk coupled to the second end of the body and passing through a cell of the stent to couple the occluder device to the stent at a second position in a section other than the annulus section.

2. The system of claim 1, wherein the disk is expandable from a collapsed configuration to a relaxed configuration.

3. The system of claim 2, wherein the disk in the relaxed configuration has a size larger than the size of at least some of the cells of the stent.

4. The system of claim 1, wherein the stent includes a plurality of struts and the fastener is coupleable to at least one of the plurality of struts.

5. The system of claim 1, wherein the body includes at least one of a metallic mesh or a shape-memory material.

6. The system of claim 1, wherein the body has an elliptical longitudinal cross-section.

7. The system of claim 1, wherein the body includes a metal mesh and polyester fiber intertwined with the metal mesh.

8. The system of claim 1, wherein the disk includes at least one of a metallic mesh or a shape-memory material.

9. The system of claim 1, further comprising a connector attached to the disk for coupling to a delivery device.

10. The system of claim 1, wherein the body includes multiple segments, each segment being capable of independent radial expansion from the other segments.

11. The system of claim 1, further comprising:
a delivery system including an outer sheath, an inner wire disposed within and translatable with respect to the outer sheath, and a connector attached to the inner wire, the connector being configured to couple the inner wire to the expandable disk of the occluder device.

12. The system of claim 11, wherein the outer sheath is adapted to house the occluder device in a contracted configuration, and the outer sheath is sized to pass through a cell of the expandable stent.

13. The system of claim 1, wherein the annulus section has a first diameter, the transition section has a second diameter, the first diameter being different than the second diameter, and the expandable disk passes through the cell of the stent in the transition section.

14. The system of claim 1, wherein the expandable body is entirely disposed between the fastener and the expandable disk.

15. A system for replacing native valve function, the system comprising:
a prosthetic heart valve having a collapsible and expandable stent forming cells, and a valve assembly disposed in the stent; and
an occluder device comprising an expandable body having a first end and a second end, the first end and the second end being disposed on opposite ends of the body, a fastener extending in a first direction and coupled to the first end of the body, the fastener capable of latching onto an apex of a cell at a first position, and an expandable disk extending in a second direction, opposite the first direction, and coupled to the second end of the body, the expandable disk passing through a cell of the stent to couple the occluder device to the stent at a second position.

16. A method for occluding a gap between a prosthetic heart valve and adjacent body tissue, the method comprising:
providing:
(1) a prosthetic heart valve having a collapsible and expandable stent forming cells, the stent having a plurality of sections including an annulus section, a transition section and an aortic section, and a valve assembly disposed in the stent; and
(2) an occluder device comprising an expandable body having a first end and a second end, a fastener coupled to the first end of the body and to a selected strut of the stent at a first position on the annulus section of the stent, and an expandable disk coupled to the second end of the body and passing through a cell of the stent to couple the occluder device to the stent at a second position in a section other than the annulus section;
delivering an occluder into an interior of the heart valve, the occluder including (i) an expandable body, (ii) a fastener coupled to one end of the body, and (iii) an expandable disk coupled to another end of the body;
advancing the occluder through a cell of the prosthetic heart valve to an outside of the heart prosthetic valve;
coupling the fastener to one end of the prosthetic heart valve; and
coupling the expandable disk to the prosthetic heart valve at a position spaced from the one end.

17. The method of claim 16, wherein the fastener is a loop and the step of coupling the fastener includes positioning the loop around an apex of a cell at the one end of the prosthetic heart valve.

18. The method of claim 16, wherein the disk in the relaxed configuration has a size larger than the size of at least one of the cells of the stent, and the step of coupling the disk includes disposing the disk on the outside of the at least one cell so that the disk cannot pass therethrough.

19. The method of claim 16, wherein delivering the occluder comprises disposing the occluder within a delivery system and advancing the delivery system into an interior of the prosthetic heart valve.

20. The method of claim 19, further comprising the step of coupling the expandable disk to an inner wire of the delivery system.

* * * * *